(12) United States Patent
Billinghurst

(10) Patent No.: US 10,877,715 B2
(45) Date of Patent: Dec. 29, 2020

(54) EMOTIONALLY AWARE WEARABLE TELECONFERENCING SYSTEM

(71) Applicant: UNIVERSITY OF SOUTH AUSTRALIA, Adelaide (AU)

(72) Inventor: Mark Nathan Billinghurst, Adelaide (AU)

(73) Assignee: UNIVERSITY OF SOUTH AUSTRALIA, Adelaide (AU)

( * ) Notice: Subject to any disclaimer, the term of this patent is extended or adjusted under 35 U.S.C. 154(b) by 113 days.

(21) Appl. No.: 16/086,187

(22) PCT Filed: Mar. 20, 2017

(86) PCT No.: PCT/AU2017/000068
§ 371 (c)(1),
(2) Date: Sep. 18, 2018

(87) PCT Pub. No.: WO2017/156570
PCT Pub. Date: Sep. 21, 2017

(65) Prior Publication Data
US 2019/0354334 A1 Nov. 21, 2019

(30) Foreign Application Priority Data
Mar. 18, 2016 (AU) ................ 2016901029

(51) Int. Cl.
*G06F 3/14* (2006.01)
*A61B 5/16* (2006.01)
(Continued)

(52) U.S. Cl.
CPC .......... *G06F 3/1454* (2013.01); *A61B 5/0002* (2013.01); *A61B 5/163* (2017.08);
(Continued)

(58) Field of Classification Search
None
See application file for complete search history.

(56) References Cited

U.S. PATENT DOCUMENTS

2009/0058660 A1  3/2009 Torch
2010/0120585 A1  5/2010 Quy
(Continued)

FOREIGN PATENT DOCUMENTS

CN  102737331  10/2012
CN  103064188   4/2013

OTHER PUBLICATIONS

International Search Report and Written Opinion prepared by the Australian Patent Office dated Jun. 1, 2017, for International Application No. PCT/AU2017/000068.
(Continued)

*Primary Examiner* — Christopher Braniff
(74) *Attorney, Agent, or Firm* — Sheridan Ross P.C.

(57) ABSTRACT

A teleconferencing system for providing remote assistance comprises a local user apparatus that captures both the field of view of the local user along with physiological state of the local user, and a remote user apparatus to allow the remote user to view what the local user is seeing and doing. The local user and remote user have a shared view and a shared audio link, and the remote user can provided assistance to the local user in performing tasks at the local site. Additionally the physiological state of the local user is monitored, and from the physiological state data, an estimate of the emotional state or physiological state of the local user is provided to the remote user. The remote user can interact or assist the local user, including controlling the amount and/or type of assistance provided to the local user based on their current emotional state.

17 Claims, 7 Drawing Sheets

(51) Int. Cl.
*G02B 27/01* (2006.01)
*A61B 5/00* (2006.01)
*G06F 3/01* (2006.01)
*H04B 1/3827* (2015.01)
*H04N 5/445* (2011.01)
*H04N 7/18* (2006.01)

(52) U.S. Cl.
CPC .......... *A61B 5/165* (2013.01); *A61B 5/7264* (2013.01); *G02B 27/0172* (2013.01); *G06F 3/013* (2013.01); *G06F 3/015* (2013.01); *H04B 1/385* (2013.01); *H04N 5/445* (2013.01); *H04N 7/185* (2013.01); *G02B 2027/014* (2013.01); *G02B 2027/0138* (2013.01); *G06F 2203/011* (2013.01); *H04B 2001/3866* (2013.01); *H04N 7/181* (2013.01)

(56) References Cited

U.S. PATENT DOCUMENTS

| | | |
|---|---|---|
| 2012/0113209 A1 | 5/2012 | Ritchey et al. |
| 2012/0143693 A1 | 6/2012 | Chung et al. |
| 2012/0242698 A1* | 9/2012 | Haddick ............... G06F 3/011 345/633 |
| 2013/0063550 A1 | 3/2013 | Ritchey et al. |
| 2013/0137076 A1 | 5/2013 | Perez et al. |
| 2014/0089399 A1* | 3/2014 | Chun .................... G06Q 50/01 709/204 |

OTHER PUBLICATIONS

"Eye Tracking: The Complete Pocket Guide," iMotions Inc., [online] Feb. 2016, 32 pages.
"Tobii Pro Glasses 2," Tobii AB, 2015, 8 pages [retrieved online from: web.archive.org/web/20160312161354/www.tobiipro.com/product-listing/tobii-pro-glasses-2/].
Picard et al. "Toward Machine Emotional Intelligence: Analysis of Affective Physiological State," IEEE Transactions on Pattern Analysis and Machine Intelligence, Oct. 2001, vol. 23, No. 10, pp. 1175-1191.
Vyzas "Recognition of Emotional and Cognitive States using Physiological Data," Massachusetts Institute of Technology, Jun. 1999, Bachelors Thesis, 85 pages [retrieved online from vismod.media.mit.edu/tech-reports/TR-510.pdf].

* cited by examiner

EMOTIONALLY AWARE WEARABLE TELECONFERENCING SYSTEM

CROSS REFERENCE TO RELATED APPLICATIONS

This application is a national stage application under 35 U.S.C. 371 and claims the benefit of PCT Application No. PCT/AU2017/000068 having an international filing date of 20 Mar. 2017, which designated the United States, which PCT application claimed the benefit of Australian Provisional Patent Application No. 2016901029 titled "AN EMOTIONALLY AWARE WEARABLE TELECONFERENCING SYSTEM" and filed on 18 Mar. 2016, the disclosures of each of which are hereby incorporated by reference in their entirety.

TECHNICAL FIELD

The present disclosure relates to teleconferencing system for remote assistance, supervision or collaboration. In a particular form the present disclosure relates to the use of an emotionally aware teleconferencing system.

BACKGROUND

Teleconferencing systems can be used to provide remote assistance or remote supervision by allowing a local user to connect to a remotely located expert over a video connection, and attempt to recreate the experience of working face to face or side by side. However when working face to face, each partner can see what their partner is doing and can estimate how they are coping through the sharing of both verbal and non-verbal cues. Studies on desktop face to face teleconferencing systems in which users actively shared their emotions self reported that they felt they had an improved understanding of each other's emotions and that emotion sharing was positively correlated to the perceived intensity of positive emotions after collaboration. This information can then be used to determine when and how much assistance to provide. However creating effective teleconferencing systems and in particular remote assistance systems has proven difficult. In one teleconferencing system for providing remote assistance for equipment maintenance or troubleshooting, a camera is held or worn by the user to allow the remote expert to see what the remote user is viewing or doing. Coupled with an audio link, the remote user can then provide assistance or guidance to the local user to assist them in conducting the equipment maintenance or troubleshooting task. In another variant two tablets are used to create a merged reality teleconferencing system. The local user places their tablet in a position to focus on the activity they are performing and in their field of view so as to allow them to see the screen and the task. This video is streamed to the remote user's tablet, who then places their hand in front of their tablet's camera or annotates the display to point out specific features or demonstrate how to perform a task, and this image or video stream is overlaid or merged onto the local user's display.

However one problem with such systems is that as the camera is outward facing with respect to the local user or otherwise directed on the task and thus the remote expert cannot determine what the user is actually focusing on or pick up visual clues that may be apparent with a face to face system. As a result situations can arise when the assistance provided may not be appropriately timed which may have the side effect of annoying the local user if they were about to perform the suggested task, or the assistance may not be noted by the local user leading to frustration of the remote user that they are being ignored, and thus the quality of the collaboration is often low compared to a face to face collaboration. In one study the use of a head mounted display with an eye tracking system by a local user was compared with a wide angle scene camera viewing the user. In this study the results indicated that the assistance provided using the wide angle scene camera was significantly better than the system using the head mounted display with an eye tracking system, although this may have been partially due to the difficulty with the quality of the eye tracking system used. However to date there has been little further research on the use of eye tracking systems and their effectiveness. In general a problem with most remote teleconferencing systems is that the remote user is only provided with limited information on what the local user is concentrating on and limited verbal cues on how the local user is coping or feeling as they are often focussed on completing the task at hand. There is thus a need to provide improved teleconferencing system for remote assistance or supervision that more effectively enhance the quality of the experience for both local and remote users, or at least provides a useful alternative to existing systems.

SUMMARY

According to a first aspect, there is provided a local user teleconferencing apparatus for use in a teleconferencing system for providing remote assistance to, or monitoring of, the local user by at least one remote user, the apparatus comprising:
  a wearable audio-visual module comprising:
    a wearable camera located to provide a view from the local user's perspective;
    a head mounted display;
    an eye tracking system mounted to or included in the head mounted display; and
    a headset;
  a physiological sensor module comprising one or more physiological sensors for monitoring one or more physiological parameters of the local user; and
  a wireless communications module,
  wherein the wireless communications module is configured to transmit audio-visual data from the audio-visual module and physiological data from the physiological sensor module to the remote user over a communication link.

In one form, the wireless communications module is worn or held by the local user.

In one form, the apparatus further comprises a wearable computer apparatus comprising at least one processor, at least one memory, and the wireless communications module, and the least one memory comprising instructions to configure the processor to control the wearable audio-visual module, the physiological sensor module, and the wireless communications module.

In one form, teleconferencing data comprises:
  video data from the wearable camera;
  audio data from the headset;
  eye tracking data from the eye tracking system; and
  physiological data from the one or more physiological sensors.

In one form, the computer apparatus is further configured to receive teleconferencing data audio data and display virtual annotation data from at least one remote user; and the headset is configured to represent the audio data to the local user, and the display annotation data is displayed on the head mounted display of the local user.

In one form, the wearable camera is attached to the head mounted display.

In one form, the headset and the one or more physiological sensors are included in the head mounted display, and the wearable camera is attached to or included in the head mounted display, and the one or more physiological sensors comprises at least a heart rate sensor and a galvanic skin response sensor.

In a further form, the memory comprises instructions for processing data from the one or more physiological sensors and generating emotional state data, and the teleconferencing data transmitted to the at least one remote user includes the emotional state data. In a further form processing the data comprises mapping the data from the one or more physiological sensors to one of a plurality of predefined emotional states, and transmitting the estimated emotional state. In a further form processing mapping the data from the one or more physiological sensors to one of a plurality of predefined emotional states is performed using either a neural network, a finite state machine or a machine learning implementation.

In one form, the physiological sensor module pre-processes data from the one or more physiological sensors and the pre-processed data is sent to the remote user over the communication link for further analysis to estimate the emotional state of the local user.

In one form, the one or more physiological sensors comprise one or more of a heart rate sensor, a blood pressure sensor, a temperature sensor, an electrodermal activity sensor, a pH sensor, an electrolyte sensor, a metabolite sensor, an electroencephalogram (EEG) sensor, an electromyography (EMG) sensor, an accelerometer, a motion sensor, or photo-sensors for measuring facial muscle movement.

According to a second aspect, there is provided a remote user teleconferencing apparatus for use in a teleconferencing system for providing remote assistance to, or monitoring of, at least one local user by a remote user, the apparatus comprising:

a remote user computer apparatus comprising a processor, a memory and a communications module;
a display; and
a user input device,
wherein the communications module is configured to receive teleconference data from the local user, and the display is configured to display a representation of video data from a camera worn by the at least one local user overlaid with an indication of an eye gaze direction of the respective local user generated from the received teleconference data, and a representation of the respective local user's emotional state, and the user input device is configured to allow the remote user to generate or provide annotation information which are transmitted to the respective local user for display on a head mounted display of the respective local user.

In one form, the communications module receives an estimate of the local user's emotional state generated by a local user apparatus, wherein the estimate is an emotional state selected from a plurality of predefined emotional states known to both the local user apparatus and remote user teleconferencing apparatus.

In one form, the remote user teleconferencing apparatus is configured to process data from the one or more physiological sensor to generate an estimate of the local user's emotional state.

In one form, each item of annotations information has a predefined priority level or is assigned a priority level by the remote user, and each priority level is associated with an emotional state threshold, such that if the estimated emotional state exceeds the emotional state threshold of a priority level, the annotation data associated with that priority level is hidden from the local user, and when the emotional state drops below the emotional state threshold of a priority level the annotation data associated with that priority level is display to the local user.

In one form, the remote user apparatus is configured to allow the remote user to control whether an item of annotation information is displayed based upon the respective local user's emotional state.

In one form, the display is a head mounted display worn by the remote user and the remote user teleconferencing apparatus further comprises a headset.

According to a third aspect, there is provided a teleconferencing system for providing remote assistance to, or monitoring of, at least one local user by at least one remote user, the system comprising:

a local user teleconferencing apparatus for each of the at least one local user comprising:
  a wearable camera for providing a video feed from the local user's perspective;
  a head mounted display;
  an eye tracking system mounted to or included in the head mounted display;
  a headset;
  one or more physiological sensors for monitoring one or more physiological parameters of the local user; and
  a local user computer apparatus comprising a memory, a processor and a wireless communications module, wherein the computing apparatus is worn or held by the remote user and operatively connected to the wearable camera, headset, head mounted display, eye tracking system and the one or more physiological sensors;
a remote user teleconferencing apparatus comprising:
  a remote user computer apparatus for each of the at least one remote user comprising a processor, a memory, and a communications module;
  a remote user display; and
  a user input device,
wherein each local user teleconferencing apparatus is configured to transmit teleconferencing data to the at least one remote user teleconferencing apparatus over at least one communication link and each remote user teleconferencing apparatus receiving the teleconferencing data is configured to display a representation of video data from wearable camera overlaid with an indication of an eye gaze direction of the respective local user generated from the eye tracking system, and a representation of the respective local user's emotional state generated from the one or more physiological sensors, and the user input device is configured to allow the remote user to generate one or more annotations on the display which are transmitted to the respective local user for display on the head mounted display of the respective local user.

In one form, an estimate of the local user's emotional state is generated by either the local user computer apparatus or the remote user computer apparatus, and the remote user controls whether an item of annotation information is displayed based upon the estimated user's emotional state.

In one form, an estimate of the local user's emotional state is generated by either the local user computer apparatus or the remote user computer apparatus, and each of the one or more annotations has a predefined priority level or is assigned a priority level by the remote user, and each priority level is associated with an emotional state threshold, such that if the estimated emotional state exceeds the emotional state threshold of a priority level, the annotation data associated with that priority level is hidden from the local user, and when the emotional state drops below the emotional state threshold of a priority level the annotation data associated with that priority level is display to the local user.

In one form, the local user computer apparatus comprises instructions for:

analysing, by the local user computer apparatus, data from the one more physiological sensors and estimating an emotional state of the local user; and transmitting the estimated emotional state to the remote user.

In one form, analysing, by the local user computer apparatus, data from the one more physiological sensors and estimating an emotional state of the local user comprises mapping the data from the one more physiological sensors to one of a plurality of predefined emotional states.

In one form, the local user computer apparatus comprises instructions is configured to pre-process data from the one more physiological sensors and to transmit the pre-processed data to the remote user, and the remote user computer apparatus is configured to analyse the pre-processed data to obtain an estimate of the emotional state of the local user.

According to a fourth aspect, there is provided a method for providing remote assistance to, or monitoring of, a local user by a remote user, the method comprising:

generating a representation of the local user's emotional state from one or more physiological sensors worn by the local user;

generating an eye gaze direction of the local user generated from an eye tracking system worn by the local user; and displaying, on a display apparatus, to the remote user a representation of video data from a camera worn by the local user overlaid with an indication of the eye gaze direction of the local user and the representation of the local user's emotional state.

In one form, the method further comprises:

generating, by the remote user, one or more annotations which are transmitted to and displayed on a head mounted display of the local user.

In one form, generating a representation of the local user's emotional state further comprises generating an estimate of the local user's emotional state and the remote user controls whether an item of annotation information is displayed based upon the estimated user's emotional state.

In one form, generating a representation of the local user's emotional state further comprises generating an estimate of the local user's emotional state, and each of the one or more annotations has a predefined priority level or is assigned a priority level by the remote user, and each priority level is associated with an emotional state threshold, such that if the estimated emotional state exceeds the emotional state threshold of a priority level, the annotation data associated with that priority level is hidden from the local user, and when the emotional state drops below the emotional state threshold of a priority level the annotation data associated with that priority level is display to the local user.

In one form, generating a representation of the local user's emotional state further comprises:

collecting data from the one or more physiological sensors worn by the local user;

analysing the collected data by a processing apparatus local to the local user and estimating an emotional state of the local user;

transmitting the estimated emotional state to the remote user; and generating a representation of the local user's emotional state using the received estimated emotional state.

In one form, the step of analysing the collected data comprises mapping the collected physiological data to one of a plurality of predefined emotional states.

In one form, the step of analysing the collected data comprises mapping the collected physiological data to one of a plurality of predefined emotional states using either a neural network, a finite state machine or a machine learning implementation.

In one form, the method further comprises:

collecting data from the one or more physiological sensors worn by the local user;

locally pre-processing the collected data;

transmitting the pre-processed data to the remote user;

processing, by a processing apparatus, the received pre-processed data to obtain an estimate of the emotional state of the local user.

In one form, the remote user monitors a plurality of local users and the generation steps are performed for each user, and the representation step is performed for each user.

BRIEF DESCRIPTION OF DRAWINGS

Embodiments of the present disclosure will be discussed with reference to the accompanying drawings wherein:

FIG. 4D is a diagram of user wearing a head mounted display system comprising integrated gaze tracking and facial expression detection hardware according to an embodiment.

In the following description, like reference characters designate like or corresponding parts throughout the figures.

DESCRIPTION OF EMBODIMENTS

Figure 1:
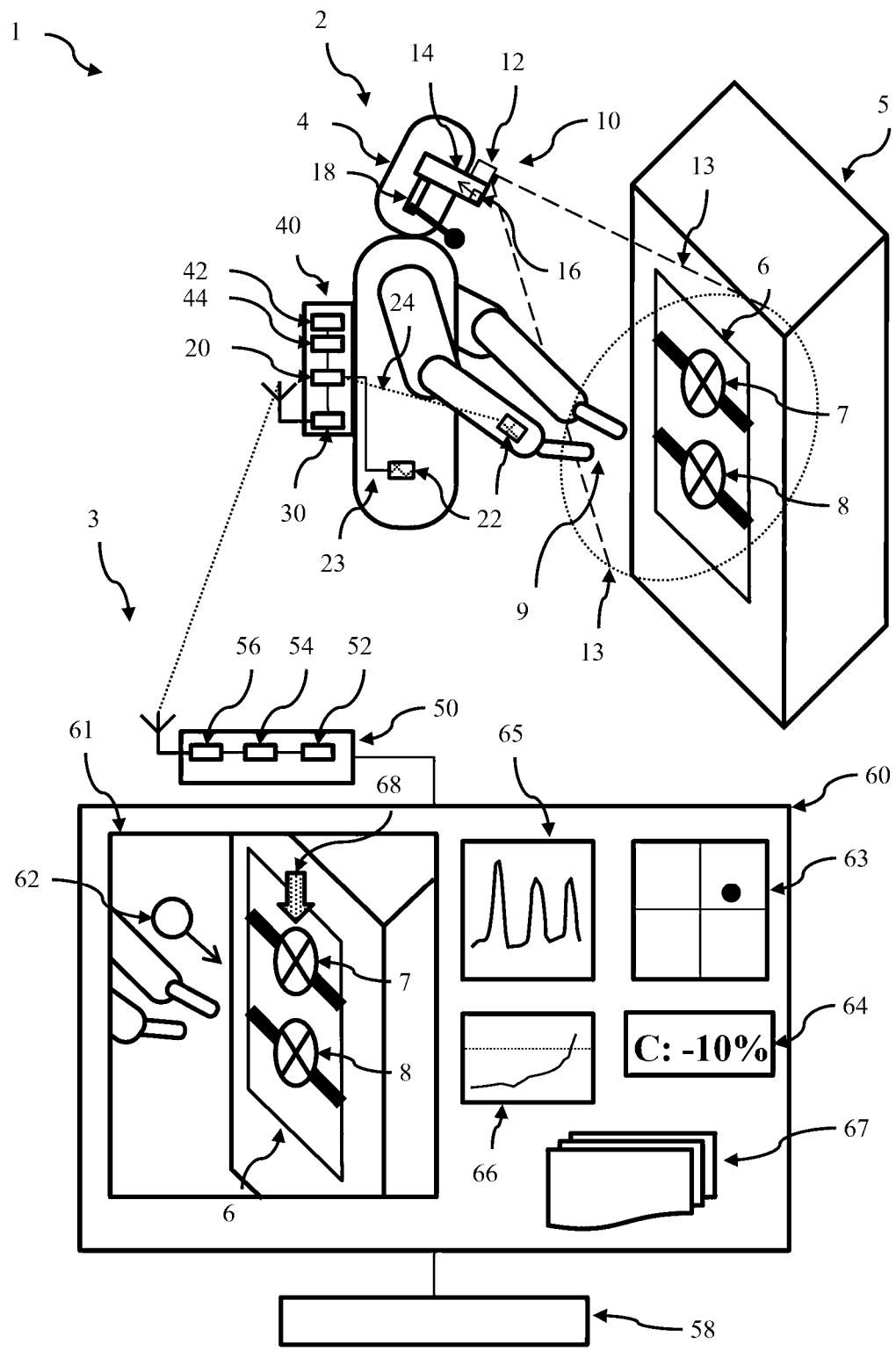
FIG. 1 is a schematic diagram of a teleconferencing system according to an embodiment.
Figure 2A:
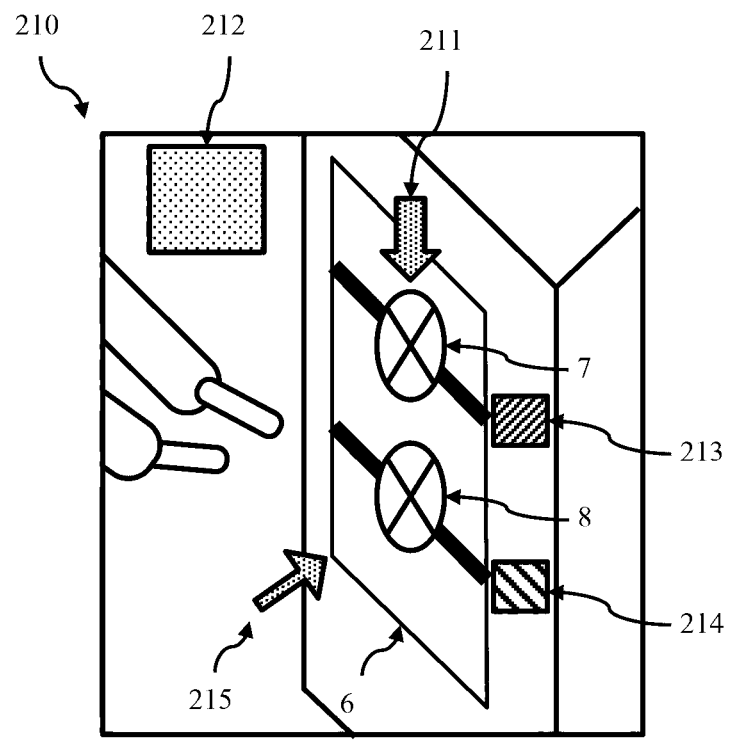
FIG. 2A is a schematic representation of a first display to a local user according to an embodiment.
Figure 2B:
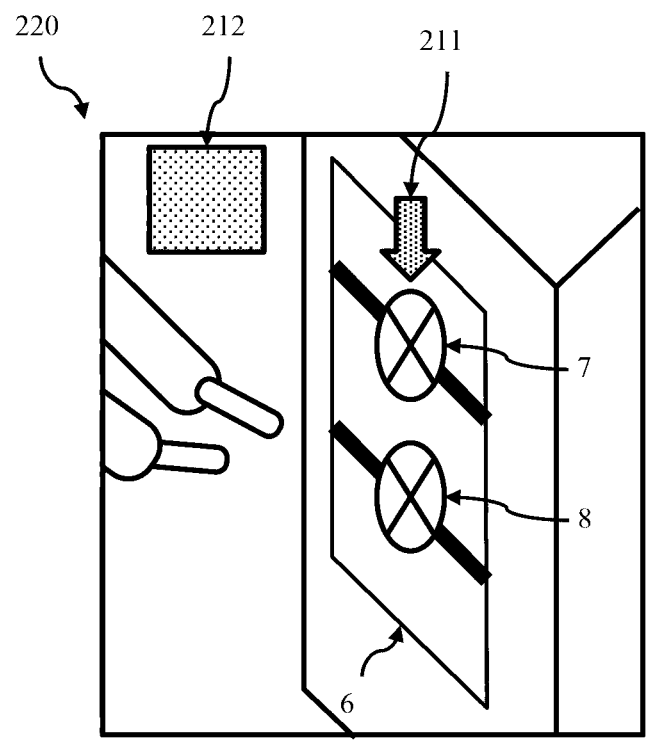
FIG. 2B is a schematic representation of a second display to a local user according to an embodiment.

Referring now to FIG. 1, there is shown a schematic diagram of a teleconferencing system 1 that can be used to provide remote assistance to, or monitoring of, at least one local user by at least one remote user, according to an embodiment. The teleconferencing system (or remote assistance system) 1 comprises a local user apparatus 2 that captures the field of view of the local user along with physiological state of the local user, and a remote user apparatus 3 to allow the remote user to view what the local user is seeing and doing. That is the teleconferencing system allows the local and remote user to have a shared view, and shared audio link. In this context the local user is user local (or proximal) to the scene being viewed by both users. Additionally the physiological state of the local user is monitored, and from the physiological state data, an estimate of the emotional state or physiological state of the local user is provided to the remote user, allowing them to empathise with the emotional state of the local user. The remote user can interact or assist the local user, including controlling the amount and/or type of assistance provided to the local user based on their current emotional state. For ease of understanding, in this embodiment a single local user is monitored or assisted by a single remote user. However it is to be understood that the system is not so limited and multiple local users could each be monitored and assisted by a single remote user (many:1), or a single local user could be monitored and assisted by multiple remote users (1:many) or some combination with multiple local users being monitored by multiple remote users with different remote users monitoring potentially overlapping subsets of the local users (many:many).

The local user apparatus 2 comprises an audio-visual module 10, a physiological sensor module 20, and a wireless communications module 30 that is configured to transmit audio-visual data from the audio-visual module and physiological data from the physiological sensor module to a remote user apparatus 3 over a communication link. The audio-visual module 10 comprises a wearable camera 12; a head mounted display 14; an eye tracking system 16, and a headset 18. The physiological sensor module 20 comprises one or more physiological sensors 22 for monitoring one or more physiological parameters of the local user. The various components of the audio-visual module may be integrated into a single device or they may be operatively connected to each other using wired or wireless links.

The wearable camera 12 provides a view 13 from the local user's perspective. In the embodiment shown in FIG. 1, a remote user 4 is working on electrical equipment 5 and has opened an access port 6 to reveal two switches 7 and 8. The view 13 captures the access port 6, switches 7, 8 and the local user's hands 9 and a representation of this view is provided to the remote user via the communications module 30. In one embodiment the wearable camera is mounted to or integrated in the head mounted display to capture a field of view aligned with the field of view of the local user. In another embodiment the wearable camera is a forward facing head mounted camera and in one embodiment this is mounted to a hat or helmet worn by the local user. In another embodiment the camera is worn on the shoulder, chest or waist of the local user and orientated to provide a forward facing view. In one embodiment the audio visual module may comprise orientation sensors such as accelerometer or tilt sensors to measure the orientation of the camera, and/or the local users head. In one embodiment the head and/or camera orientation could also be calculated from the head camera video using computer vision techniques, either alone or in conjunction with sensor data. In one embodiment the audio visual apparatus is configured to identify or determine the likely field of view of the local user within the field of view of the camera based on the relative orientation and distance of the local users head and the camera and provide this likely field of view as the representation to the remote user. This determination may be performed locally by the audio-visual module, or by another module of the local user teleconferencing apparatus, or data on the relative orientation and distance of the local users head and the camera may be transmitted to the remote user, and the determination may be performed at the remote user end.

The head mounted display 14 is configured to overlay information on the view of the user (ie an augmented reality display). In one embodiment the head mounted display is a see through display such as a display integrated in or projected onto a transparent screen located in front of the local user's eye (or eye's) such as onto a lens in a pair of glasses (eg Google Glass) or onto a monocle. In another embodiment the head mounted display is an enclosed display in which the natural view of the user is replaced with a view from a camera (or cameras) which is augmented with additional information. In one embodiment the head mounted display is a LCD, LED, OLED or similar screen (or screens) in a pair of goggles. In one embodiment the head mounted display is a virtual retina display that projects an image directly onto the local user's retina. Examples of head mounted display include the Epson Moverio BT-200 and the Brother AirScouter. The Epson Moverio is a commercial smart glass that has a stereo optical see-through display which is connected to a controller comprising a 1.2 GHz Dual Core CPU with 1 GB RAM, an 8 GB internal memory, a multi-touch screen user interface, a LiPo Battery, and runs Android OS. The display is 24 bit colour LCD display (960×540×3) with a 22.4° field of view and is perceived as a floating 80-inch screen at 5 m. The Moverio further includes USB, Bluetooth and Wi-Fi connectivity, a forward facing VGA camera, an integrated headset (microphone and speakers), GPS, and motion tracking sensors including an accelerometer, a compass, and a gyroscope in both the headset and the controller. The headset weighs around 88 g and the controller weighs around 124 g. The Brother AirScouter is a high quality optical see through monocular display connected to a control box. The display has SVGA 800×600 resolution and 22.4° field of view and is equivalent to a 40 cm display at 1 m. The display weighs around 64 g and the control box around 75 g.

In one embodiment the eye tracking system 16 is mounted to or included in the head mounted display 14. The eye tracking system is used to determine where the local user is looking within their field of view (ie their gaze direction). In one embodiment, the eye tracking system comprises a camera and an infrared (IR) or near IR emitter to create conical reflections or retinal reflections from which gaze direction can be determined. In other embodiment other eye tracking system such as retinal imagers, devices that directly measure the movement of an object attached to the eye, such as specialised contact lens, or devices that using electrodes placed around the eyes to measure the electric potentials and infer gaze direction.

In one embodiment the headset 18 comprises a microphone and at least one speaker. In one embodiment the headset is mounted to or incorporated into the head mounted display. In one embodiment the headset is a bone conduction headset. The headset may be connected to the wireless communication module via a wired or wireless connection.

In one embodiment all the components of the audio-visual module 10 are integrated into a head mounted display unit. In one embodiment the audio-visual module 10, the physiological sensor module 20, and the wireless communications module are worn by the local user. The audio-visual module 10 and the physiological sensor module 20, and/or the individual components of these modules, may be connected to the wireless communications module by wired or wireless connections (or links), and a combination of the two may be used. The wireless communication module may support multiple communications protocols, such as mobile or cellular standards (eg 4G standards), IEEE 802.11 standards including IEEE 802.15 standards including Bluetooth and personal area networks, or other proprietary communication standards. The wireless communication module may use one protocol or standard for communicating with the remote user (eg 4G or Wi-Fi), and another short range protocol (eg Bluetooth) for communicating with the audio-visual module 10 and the physiological sensor module 20, and/or the individual components of these modules.

In another embodiment the audio-visual module 10 and the physiological sensor module 20 are worn by the user, and are configured to wirelessly communicate with a wireless communications module located nearby the local user. The wireless communication module may be located on another person in the case that the local user is part of a team, in a nearby vehicle or at a base camp, or as part of wireless network infrastructure such as a local area network access point providing wireless connectivity in the area of operation of the local user.

In one embodiment a computing apparatus 40 is worn by the user and is operatively connected to each of the audio-visual module 10, the physiological sensor module 20, and the wireless communications module 30, over wired or wireless connections. In this embodiment the computing apparatus 40 comprises at least one processor 42 and a memory 44 that comprises instructions to configure the processor to control the operation of the local user teleconferencing apparatus, such as to control the head mounted display, and coordinate an audio-visual connection (or channel) with the remote user. In one embodiment the computing apparatus 40 is integrated with one or more of the modules, such as being provided on a common mother board or connected boards in a common housing. In one embodiment the computer apparatus is provided on a motherboard incorporating a processor chip, a memory, a wireless communications chip, an audio visual processing chip or graphics card, and sockets, ports or connections to one or more hardware elements such as the camera, the head mounted display, eye tracker output, headset, and physiological sensor. In one embodiment the wireless communication module is further configured to wirelessly connect to the one or more hardware elements such as the camera, the head mounted display, eye tracker output, headset, and physiological sensors. Additionally or alternatively, each of the audio-visual module, the physiological sensor module and the wireless communications modules comprise at least one processor and a memory containing instructions to configure the operation of the respective module and/or communication with the other modules. In one embodiment at least one processor is an embedded or real time microprocessor. In one embodiment the computational tasks are distributed between the modules.

The audio-visual module sends audio-visual data to the remote user over a communications link established by the wireless communications module. The audio visual data includes video data from the camera, audio data from the headset, and eye tracking data from the eye tracking system. The teleconferencing software at the remote user provides a representation of the camera view and audio to the remote user along with the eye tracking data. The audio visual module is further configured to provide display sharing between the head mounted display of the local user and display device of the remote user. This allows the remote user to generate or provide annotation information which is send back to the local user over the communication link and displayed on the local user's head mounted display. For example the remote user could observe where the local user is looking, and draw a virtual circle around a specific component to be checked, or place a virtual arrow near a specific feature. Additionally the remote user could look up a manual or specification for a specific component the local user is testing, and the remote user could paste the acceptable range or reference data on the display to allow the local user to compare or interpret test results or status. Audio data from the remote user can also be provided along with annotation data.

One problem with existing teleconferencing apparatus for providing remote assistance to a local user by a remote user is that the remote user only has access to the field of view of the user and any verbal communications. As the remote user cannot see the person or their face they lack many of the non-verbal clues available in face to face interactions and it is very difficult for them to assess how the local user is coping with their situation (ie their level of stress) or what they are feeling (confident, unsure, fatigued, etc). Locating a camera in front of the local user's face to capture such visual clues is often not practical, especially when the local user is attempting to perform active tasks, or moving around the environment. Additionally providing an additional view of the user's face occupies further bandwidth and cognitive load on the remote user in interpretation of facial clues. To address this issue and to enable the remote person to have an increased understanding of what a local user is doing and feeling (ie to allow them to empathise with them), the local user apparatus 2 comprises a physiological sensor module 20 that comprises one or more physiological sensors 22 for monitoring one or more physiological parameters of the local user. The physiological data from the physiological sensor is sent to the remote user to enable an assessment of the local user's emotional and/or physiological state. The physiological data may be sent in either a raw or processed form, and may be further processed by the remote user.

A range of physiological sensors 22 may be used to measure a range of physiological parameters, or to provide multiple measurements of the same parameter. The physiological sensor data is used to obtain an estimate of the emotional state of the local user. In the context of this specification, emotional state is used in an inclusive sense to include both physiological state and emotional state inferred from physiological data. That is the physiological state may be directly indicative of an emotional state, or an emotional state may be determined or inferred from physiological data. In this context the physiological sensors could broadly be considered emotion monitoring sensors. That is they collect data from a person (user/wearer) which can be processed/analysed to estimate or determine an emotional state of the person (user/wearer). The physiological sensors 22 may include one or more of a heart rate sensor, a blood pressure sensor, a temperature sensor, an electrodermal activity sensor (also known as a skin conductance or galvanic skin response sensor), a pH sensor, a sweat composition sensor, an accelerometer, a motion sensor, an orientation sensor, a microphone, a camera, an electroencephalogram (EEG) sensor, an electromyography (EMG) sensor, etc. The physiological sensors may be distributed around the body, be worn or held, or may be integrated in the head mounted display. These sensors may be standalone sensors, or integrated with other components (ie components may be used to provide more than one function). For example a camera in an eye tracking system could also be used to detect and report pupil size (in addition to tracking gaze). Absolute pupil size and temporal changes in pupil size could be used or processed to estimate the physiological state of the local user. For example as a person gets scared their pupil size widens. Similarly in addition to providing the audio stream from the microphone in a headset to the remote user, the audio stream could be processed to detect stress or other emotions in the local users voice. Various physiological sensors will now be described.

Motion or orientation sensors such accelerometers, tilt sensors, gyroscopes, vibration sensors, stretch/linear extension sensors, strain sensors, photo-sensors (including light based emitter/receiver pairs) etc, can be used in a variety of ways. Motion or orientation sensors can be used to measure muscle movements around the face and eyes can also be used to infer facial expressions and thus emotional state. Motion sensors may also capture gross body movements such as shaking of the head, movements of the arms, as well as finer scale movements such as involuntary tremor or fine shaking of hands or muscles that may indicate fatigue or another physiological and/or emotional state.

Photo-sensors mounted on glasses or a similar frame can be used to measure facial muscle movement such as skin deformation around the eye caused by facial expression change. Photo reflective sensors measure the distance between the module and skin surface on face and are small enough to fit on a wearable device, are unobtrusive, and the signals can be the processed fast enough for real-time prediction of the facial expression or emotional state. The facial expression or emotional state can then be displayed or visualised by the remote user. Estimation of the facial expression or emotional state may be performed locally (for example by an Arduino microcontroller running a machine learning algorithm trained on the user) in which case only data representing the emotional state needs to be sent to the remote user, or sensor data may be sent to the remote user for processing and estimation of the facial expression or emotional state.

Heart rate sensors measure heart rate, which can be analysed to measure additional parameters such as the heart rate variability which is an indicator of mental effort and stress in adults. Analysis of heart rate information can also be used to differentiate between positive and negative emotions. Heart rate variability (HRV) refers to the oscillation of heart rate and has been used as an indication of mental effort and stress in adults. Further signal analysis such as spectral analysis or time-frequency analysis of heart rate data can also be used to determine emotional cues.

Electrodermal activity sensors (also known as a skin conductance or galvanic skin response sensor) measure the sweat response such as by measuring skin resistance (or conductance), which varies with the state of sweat glands in the skin. Sweating is controlled by the sympathetic nervous system, and so skin conductance is an indication of physiological state and emotional/psychological arousal. For example when a person is stressed or excited, their autonomic nervous system becomes aroused and sweating increases, leading to an increase in skin conductance. Thus by measuring the skin conductance a measure of the emotional state of the local user can be estimated. Additionally or alternatively, measurements of the pH of sweat or the composition of sweat can be used. The pH of sweat is normally around 7, but as people exercise the rate at which sweat is excreted increases leading to an increase in the pH of sweat (this is thought to be due to the sweat ducts having less time to reabsorb sweat constituents). Sweat composition sensors can be also used to measure electrolytes (eg sodium, chlorine, and potassium), metabolite levels (eg lactic acid, glucose, uric acid, etc) and other small molecules and proteins found in sweat. Analysis of the composition can be used to indicate the level of hydration and/or fatigue.

Analysis of physiological data from one or more physiological sensors can be analysed to estimate the emotional state of the local user. The emotional and/or physiological state may be estimated from analysis of specific sensor data and may use publically available or proprietary analysis algorithms. In some embodiments sensor data from multiple sensors may be combined to provide an overall measurement of emotional state. Examples include the Q sensor by Affectivia (Waltham, Mass.) and the XOX wristband by XOX Emotional Technologies/XOVIA of London. Both systems use wristbands (although the sensors could be worn in other locations such as the body or head) and estimate stress/excitement levels from measurements of skin conductance. Another example is the Spire sensor (Spire—http://www.Spire.io, San Francisco) which is worn on the hip or torso and measures movement and respiration patterns. Data is wirelessly transmitted to an analysis module. The Spire measures over 10 characteristics of each breath cycle such as frequency and magnitude of breaths, and the ratio of in to out, and analysis software recognises different types of breathing patterns so that alerts to the user can be generated. Another example is the ECHO and H2 Smart Patch manufactured by Kenzen (http://www.kenzenwear.com/) that provides a continuous measure of hydration, lactic acid and glucose analysis from composition analysis of sweat. The H2 Smart Patch comprises an adhesive patch that may be stuck on the abdomen or another part of the body and contains a paper microfluidic layer that wicks sweat past sensors. The sensors are externally powered and wirelessly transmit data to a receiver module. Iontophoresis may also be used to actively extract sweat from the skin. In another example, the Sensaura analysis suite provided by Sensaura Tech (http://www.sensauratech.com/) analyses data from heart rate sensors and electrodermal activity sensors to provide an estimate of the emotional state of the user.

In some embodiments the physiological data is sent to the physiological sensor module 20, and is then transmitted to the remote user for analysis via the communications module 30. The connection between the physiological sensor module 20 and the physiological sensors 22 may be wired 23 or wireless 24 or some combination such as wireless to communication module 30 and wired from the communication module 30 to the physiological sensor module 20. In some embodiments, the physiological sensor module performs pre-processing of the physiological data, such as averaging, applying transforms (eg wavelet or Fast Fourier Transforms), normalisation, etc, and the pre-processed data is send to the remote user for further analysis. In some embodiments the physiological sensor module performs local analysis of the physiological data, and an estimate of the emotional or physiological state is sent to the remote user. The physiological sensor module 20 may be a software module (instructions) stored in memory 44 and executable by processor 22 or comprise a separate electronic circuit and/or processor and memory.

Referring back to FIG. 1, a remote user teleconferencing apparatus 3 is configured to allow a remote user to monitor and provide assistance to the local user. The remote user apparatus 3 comprises a remote user computer apparatus 50 comprising a processor 52, a memory 54 and a communications module 56. The remote user teleconferencing apparatus 3 further comprises a display 60 and a user input device 58 (or devices) such as mouse and keyboard, a touch sensitive device such as a tablet with multi-touch input, a wearable user input device such as a glove or gloves, etc. The display may be a LCD or LED flat screen display, a touch enabled screen (in which case the display may also function as a user input device), a 3D display, a head mounted display such as display goggles (2D or 3D) or a see though display, or other similar display devices.

The communications module 56 is operatively connected to the local user communications module 30. In this embodiment the communications module 56 is a wireless communication module that communicates with the local user communication module 30 over a wireless network (not shown). In other embodiments the communications module comprises a wired (e.g. Ethernet) connection to a gateway which is operatively connected to a wireless access point in communication with local user communication module 30. The memory comprises instructions to configure the processor to execute software modules to establish and support the teleconferencing session between the local and remote user apparatus. The communications module 56 is configured to receive teleconference data from the local user, and the display 60 is configured to display a representation 61 of video data from the camera 12 worn by the local user 2. Audio data from the local user is output by the computing apparatus using an internal speaker or is output by external speakers or a headset connected to the computing apparatus. Similarly audio input from the remote user can be received by a microphone integrated into the computing apparatus, or a microphone in a headset worn by the remote user. Audio data received from the remote user is then sent to the local user by the communications module.

In the embodiment shown in FIG. 1, a remote user 4 is working on electrical equipment 5 and the remote user 4 has opened an access port 6 and can view two switches 7 and 8. The camera 12 captures a view 13 of the access port 6, switches 7,8, and the local users hands 9 which is sent to the remote user apparatus 3 and a representation 61 is displayed on the remote user display 60. The representation 61 provides a view from the local user's perspective. In one embodiment the video data is a substantially live stream from the camera. In one embodiment the video data is sent between the local user apparatus and remote user apparatus in a compressed format in order to conserve bandwidth. The representation is a reduced portion of the camera field of view, a transformed version (e.g. changed aspect ratio), or comprises a zoomed in portion. The display is further overlaid with an indication of an eye gaze direction 62 of the local user. The gaze direction may be determined by the eye tracking system 16 at the local user side, or may be generated at the remote user side from the eye tracking data provided by eye tracking system 16. In this way the remote user can simultaneously view what the local user is seeing, and where they are directing their attention.

Additionally the remote user apparatus 3 displays a representation of the local user's emotional or physiological state 63. The representation may be a single representation to summarise the emotional state, or it may comprise multiple representations which may be representations based on different physiological sensor or combinations of sensors or processed sensor outputs. The representation may also be indicating a change in emotional state (eg from calm to stressed, or calming down). In this embodiment the emotional state is plotted on a 2D chart separated into zones indicative of different states. In one embodiment the x axis is indicative of stress with relaxed on the left and increasing stress on the right and the y axis is indicative of self-confidence with negative values indicative of a negative attitude (e.g. lacking confidence) and positive values indicative of positive attitude (e.g. confident). In this embodiment the local user is under stress, but still feels confident in their ability to handle the task. In other embodiments, other emotional representations may be used such as faces, emoticons, symbols, descriptive words or tags, or descriptions. In this embodiment an emotional change indicator 64 is shown which indicates a percentage change in emotional state over a predefined time period such as the last 5 minutes. In this embodiment the value of −10% indicates a decline in the confidence (C) which indicates that the user is struggling to cope with the situation. Various change indicators could be displayed using numerical percentage), colour based (e.g. heat maps) or graphical indicators (e.g. arrows). In this embodiment physiological sensor data such as a heart rate plot 65 and sweat conductance plot 66 are also illustrated. Additional information 67 regarding the system the local user is accessing may also be displayed, such as manuals, schematics, procedure manuals etc, that the remote user can use to provide assistance to the local user. A screen sharing utility may be used to share material viewed by the remote user with the local user. For example this may allow the remote user to select a window or frame on their desktop to be shared with the local user.

Further the user input device 58 is configured to allow the remote user to generate annotations 68 on the display 60 which are transmitted to the local user for display on the head mounted display 14 of the local user. In this embodiment the remote user provides an arrow pointing to the first switch 7 that the local user should be testing, rather than the second switch 8 that the user if focussing on as indicated by the gaze indication (62).

The teleconferencing system enables the remote user to monitor what the local user is seeing and doing whilst also providing them information on the physiological and emotional state of the local user. This is achieved without requiring a camera focussed on the user's face and in any event can provide additional cues about how the user is actually coping, typically far beyond that available from voice and facial cues. In this way the remote user can more closely monitor how the user is coping and decide on the level of assistance to be provided. Further the physiological data used to infer emotional state occupies significantly less bandwidth compared to the audio-visual data, and significantly less bandwidth than would be required by an additional face directed camera, and so does not place a significant power or computational load on the local user apparatus. Analysis may be performed at the remote user side which will typically have greater power and computational resources than those available with the local user. Various approaches may be used to combine or represent physiological data from multiple sensors into a single emotional indicator or representation. In one embodiment, a set of standard emotional states may be defined, and each sensors data is then mapped to a standard emotional state. In the case of individual mapping the emotional states may be combined or averaged to obtain a final estimate of the emotional state (and an uncertainty) or the sensor data may be collectively mapped to a standard emotional state. Sensor mappings may be obtained by using a calibration process or a machine learning technique such as supervised learning. Each emotional state may be assigned a numerical value and optionally an uncertainty and multiple emotional states may be summarised using a summary statistic such as an average (including standard, trimmed, weighted, and robust variants). Alternatively the system could be trained or configured to combine data using a more sophisticated algorithms such as neural networks, finite state machine (e.g. Hidden Markov Model approach) or machine learning (e.g. clustering, supervised learning, etc). These approaches may require training to determine how data should be combined.

In one form, the remote user apparatus 3 is configured to allow the remote user to control whether an item of annotation information is displayed based upon the users emotional state. Thus as the user's stress level increases, or confidence or coping level decreases, the remote user may reduce the amount of additional information provided to the local user to reduce the cognitive load. This is illustrated in FIGS. 3A and 3B. FIG. 3A is a schematic representation of the head mounted display 210 of the local user comprising annotation information provided by the remote user to the local user. In this embodiment 5 items of annotation information, 211, 212, 213, 214, and 215 are overlaid on the local user display to provide information about the system the local user is working on. If the remote user determines the user is overstressed or struggling to cope, the remote user can reduce the amount of annotation information provided. FIG. 3B shows a second display 220 in which the amount of annotation information has been reduced to two items 211 and 212.

The control of the virtual annotation information may be manually performed by the remote user, or it is performed in a semi-automated or automated way. When adding annotation information the remote user can assign a priority level or category to the information, or this may be predefined. The remote user can also set various emotional state thresholds that places limits on when a given priority level or category may be displayed, as well as a limit on the amount of any one priority level or category. As stress/coping thresholds are crossed the system may automatically remove annotation data, or, in the case of a semi-automated system the remote user may be asked whether information should be removed and/or which should be retained. Similarly as the local user reduces stress or is coping better and drops below a threshold, previously hidden annotation data may be added back in. That is, each annotation has a predefined priority level or is assigned a priority level by the remote user, and each priority level is associated with an emotional state threshold. If the estimated emotional state exceeds the emotional state threshold of a priority level, the annotation data associated with that priority level is hidden from the local user, and when the emotional state drops below the emotional state threshold of a priority level the annotation data associated with that priority level is display to the local user.

Figure 3:
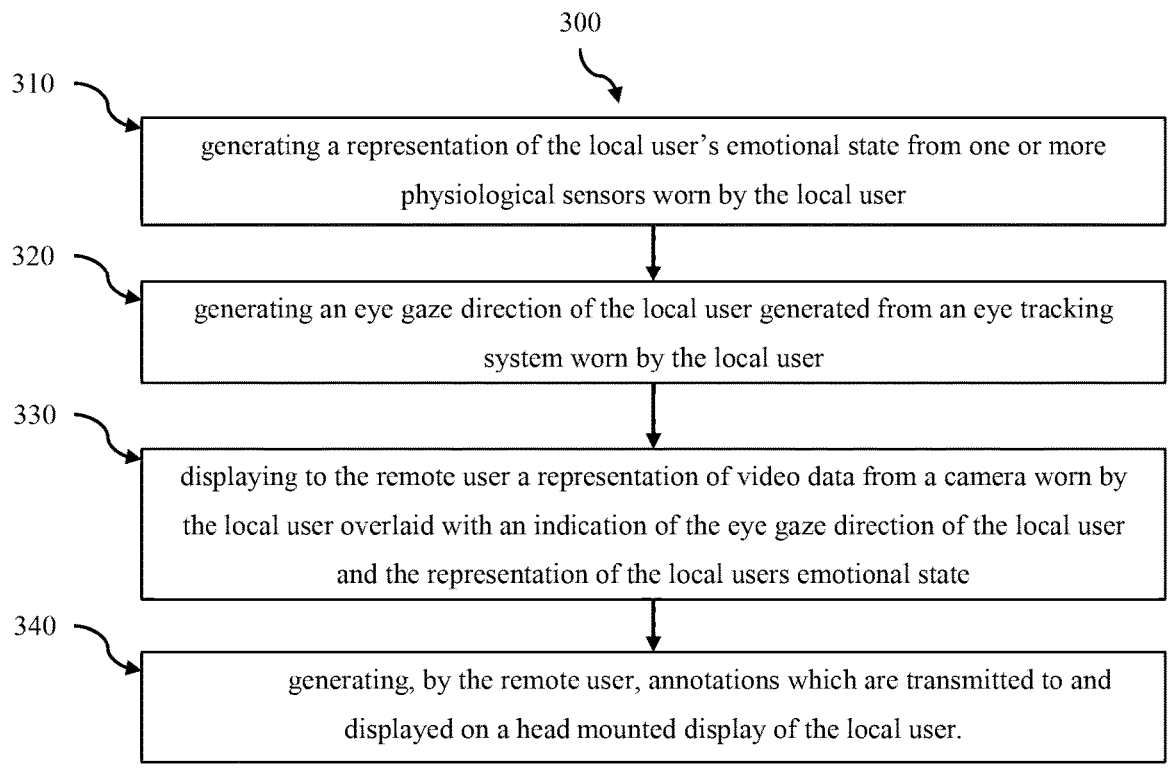
FIG. 3 is a flowchart of a teleconferencing method according to an embodiment.

FIG. 3 is a flowchart 300 of a teleconferencing method for providing remote assistance to, or monitoring of, a local user by a remote user according to an embodiment. At step 310 a representation of the local user's emotional state from one or more physiological sensors worn by the local user is generated. At step 320 the eye gaze direction of the local user is generated from an eye tracking system worn by the local user. Step 330 comprises displaying to the remote user a representation of video data from a camera worn by the local user overlaid with an indication of the eye gaze direction of the local user and the representation of the local users emotional state. An option step 340 comprises generating, by the remote user, virtual annotations which are transmitted to and displayed on a head mounted display of the local user.

The above method and variations as described herein can be provided as a computer program product comprising containing instructions executable by a processor. The system may be a computer implemented system comprising of a display device, a processor and a memory and an input device. The memory may comprise instructions to cause the processor to execute a method described herein. The processor memory and display device may be included in a standard computing device, such as a desktop computer, a portable computing device such as a laptop computer or tablet, or they may be included in a customised device or system. The display devices may be head mounted display devices. The computing device may be a unitary computing or programmable device, or a distributed device comprising several components operatively (or functionally) connected via wired or wireless connections. The local and remote computing apparatus 40 50 may comprise a central processing unit (CPU) further comprising an Input/Output Interface, an Arithmetic and Logic Unit (ALU) and a Control Unit and Program Counter element which is in communication with input and output devices through the Input/Output Interface. The Input/Output Interface may comprise a network interface and/or incorporate the communications module for communicating with an equivalent communications module in another device using a predefined communications protocol (e.g. Bluetooth, Zigbee, IEEE 802.15, IEEE 802.11, TCP/IP, UDP, etc). A graphical processing unit (GPU) may also be included. The computing device may be a single CPU (core), multiple CPU's (multiple cores), or comprises multiple processors. The computing device may use a parallel processor, a vector processor, or be a distributed computing device. The memory is operatively coupled to the processor(s) and may comprise RAM and ROM components, and may be provided within or external to the device. The memory may be used to store the operating system and additional software modules or instructions. The processor (s) may be configured to load and executed the software modules or instructions stored in the memory to implement the method.

Figure 4A:
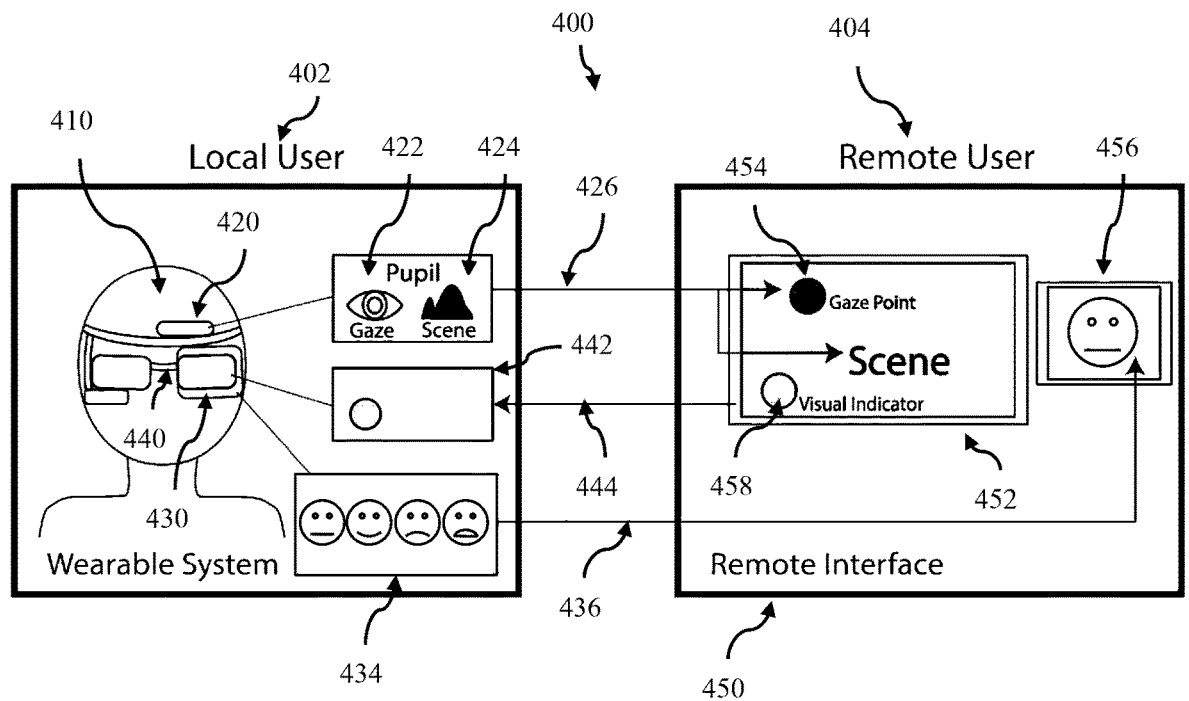
FIG. 4A is schematic diagram of an embodiment of a system.
Figure 4B:
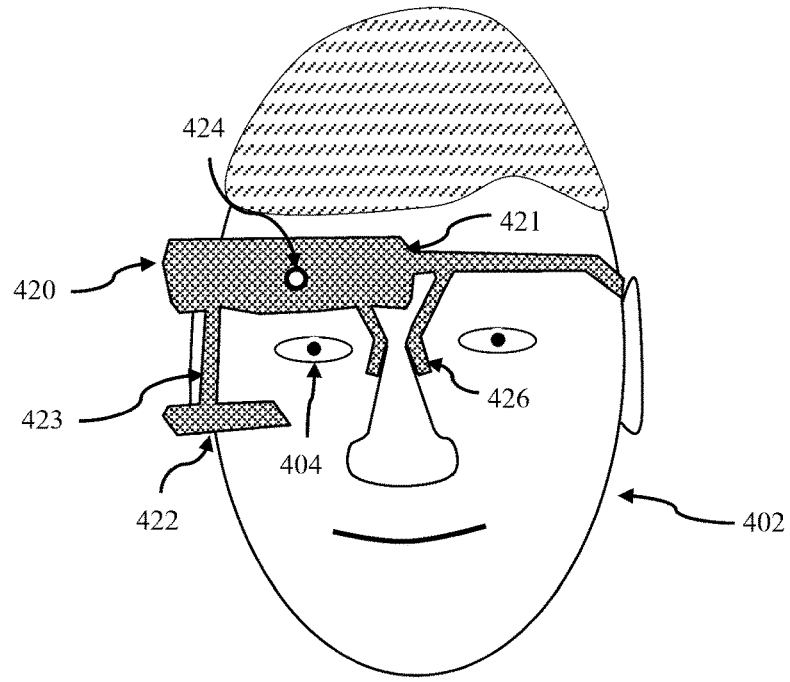
FIG. 4B is diagram showing gaze tracking hardware worn by a user according to an embodiment.

FIG. 4A is a schematic diagram of an embodiment of a system 400 in which a local user wearable apparatus 410 worn by a local user 402 captures and send the local user's view point, gaze and facial expression to a remote user interface 450 where the received information is viewed by a remote user 404 who can annotate the video (or visual) feed which is sent back to the local user and displayed in a head mounted display (HMD). The local user wearable apparatus 410 comprised a Pupil eyetracker 420 which recorded the estimated the gaze of the user 422 and the wearer's view or scene 424, a facial expression sensor module 430 which provided an estimate of the emotional state of the user 432, and an Epson Moverio BT-200 head mounted display (HMD) 440 comprising frame 441 and see through displays 442. The remote user interface 450 displayed the wearers view (scene) 452 and the estimated gaze point of the local user 454 on the scene 452. A representation of the emotional state 456 based on the facial expression data was displayed adjacent the scene 452 in the form of an emoticon image. The remote user interface allowed the user to provide annotation data on the camera feed in the form of a visual indicator 458. The scene and visual indicator annotated video feed is sent back to the local user and displayed by the Epson Moverio 430 worn by the user.

The Pupil eyetracker 420 is an open source platform for pervasive eye tracking and mobile gaze-based interaction. It uses two cameras mounted to a frame 421. The first camera is an eye camera 422 to track the user's right eye 404 gaze and a scene camera to capture the user's view 424. The eye camera was located below the user's right eye via a support 423 extending down from the frame 421 which supported the scene camera 424. The Pupil hardware can track the eye gaze 424 with 0.6° accuracy at a 120 Hz capture rate, and has a full HD scene camera with 5.7 ms latency. Software tracks the eye pupil in the video stream and maps or overlays the eye gaze direction 454 on the scene camera video stream 452 which is sent to the remote user 404 over link 426. The video feed or stream 452 was displayed to the remote user 404 via in the remote user interface 450 with the gaze 454 indicated as a red dot. A green circle indicator 458 followed the remote user's mouse input to allow the remote user (helper) to provide visual pointing feedback on the live camera view of the local user. The live camera view with the remote user indicator (the green dot) was sent back to the local user via link 444 for display to the local user 402 by the Epson Moverio HMD 440 worn by the local user.

Figure 4C:
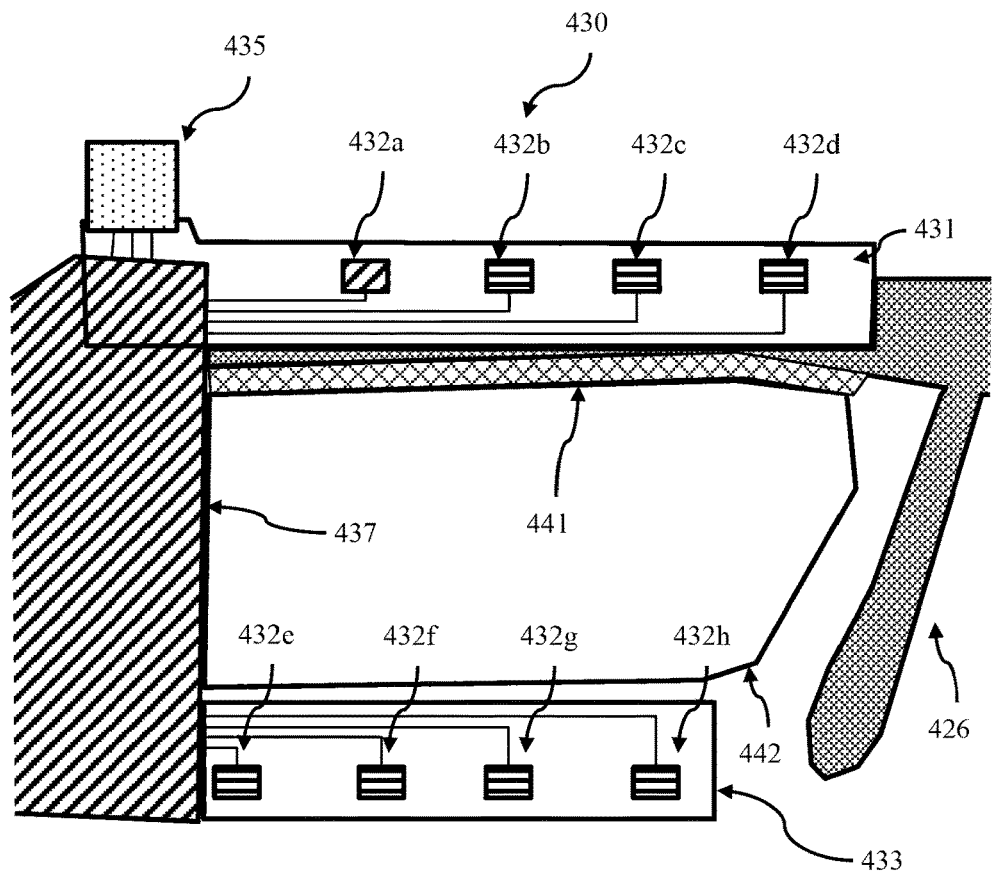
FIG. 4C is diagram showing sensor placement for detection facial expressions on the inside of a frame according to an embodiment.
Figure 4D:
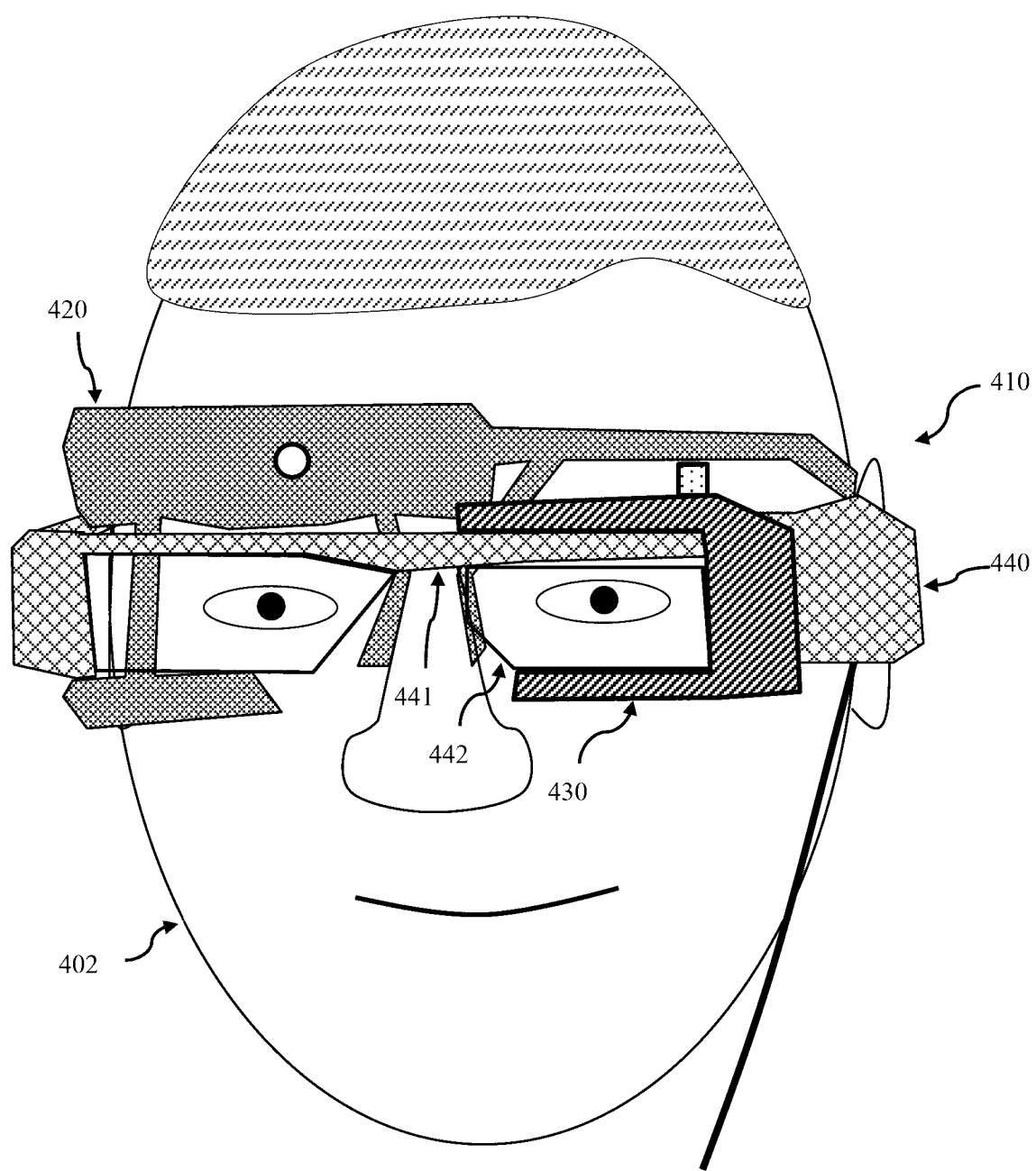
FIG. 4D is a diagram of a local user wearing a local user apparatus according to an embodiment.

The facial expression sensor module 430 was developed based upon the AffectiveWear (AW) module and comprised an Arduino Fio, eight photo reflective sensors (SG-105), a transistor (IRLU3410PBF), Xbee, and Li-Po battery. FIG. 4C is figure showing sensor placement for detection facial expressions on the inside of a frame (ie eye side) according to an embodiment. The module was secured to the frame of the left lens of the Epson BT-200 Head Mounted Display (HMD) with four sensors 432a 432b 432c 432d on top of the display on upper support 431 and the other four sensors 432e 432f 432g 432h are placed below the display on lower support 433. The sensors 432 were connected to the transistor 435 and the Arduino Fio (not shown) via connector 437. Changes in facial expression cause skin deformation in the area around the eye and the photo reflective sensors 432 measure the distance between the module and skin surface on face. The signals from the photo reflective sensors was processed by a machine learning algorithm executing on the Arduino Fio to identify a facial expression from a set of facial expressions 434. In this embodiment the set of facial expressions were four facial expressions representing (Neutral, Positive, Negative, Surprise) although in another embodiment a wider range of facial expressions could be recognised. In this embodiment the machine learning algorithm was trained on a set of posed facial expression by the user for each emotional label. However in other embodiment a more robust algorithm could be used which did not require individual user training. The estimated expression data (cg neutral) was sent to the remote user at around 170 frames per second over link 436, and was displayed or visualized to the remote user using an emoticon face 456 corresponding to the estimated facial expression (from set 434). FIG. 4D is a drawing of a local user 402 wearing an embodiment of the local user wearable apparatus 410. The Epson BT-200 Head Mounted Display 440 acts as a support for the sensors of the facial expression detection module 420 and is flanked by the frame and cameras of the Pupil eyetracker 420. The frames of the head mounted display and pupil eye tracker are secured to each other.

A user study yeas conducted using the system illustrated in FIGS. 4A to 4D to investigate how the emotional state representation (from the physiological data) affected remote collaboration. Four different interface conditions (treatments) were tested. In each case the local user and remote user were able to talk (and listen) to each other. The first condition was a video only condition in which the remote user can only see video from the local user (V). The second condition was a video plus pointer condition, which is the same as the V condition with the addition of gaze cues and pointing on the head worn camera (HWC) video (P). The third condition comprised a video plus expression condition which is the same as the V condition with the addition of the facial expression monitor (E) and the fourth condition was an all data condition which adds both pointing, gaze tracking and facial expression to the V condition (A).

The task presented to the users was to work together to construct 2D pictures of various objects (eg sports car, castle, cruise liner and animal) out of wooden blocks. This is similar to earlier physical construction tasks used in remote collaboration studies. A within subjects design was used where pairs of users would use each of the four different interface conditions with a different object for each condition. The order of the conditions and the objects were counterbalanced to reduce any order effects. Subject pairs were given five minutes to construct a picture for each condition and were told that they should try and use as many of the blocks as possible. Before the experiment began calibration of the head mounted hardware was completed to obtain eye gaze and facial expression settings for the local user. After each condition they were asked a number of Likert scale questions about how well they thought they worked together, could understand each other, and communicated together, etc. These were asked on a scale of 1 to 7, where 1=strongly disagree and 7=strongly agree. After all the conditions were over they were asked to rank each interface in order according to how well they communicated with their partner, and worked together, etc. Observation of the subject behaviour was made and the subjects were interviewed after the experience.

Figure 4E:
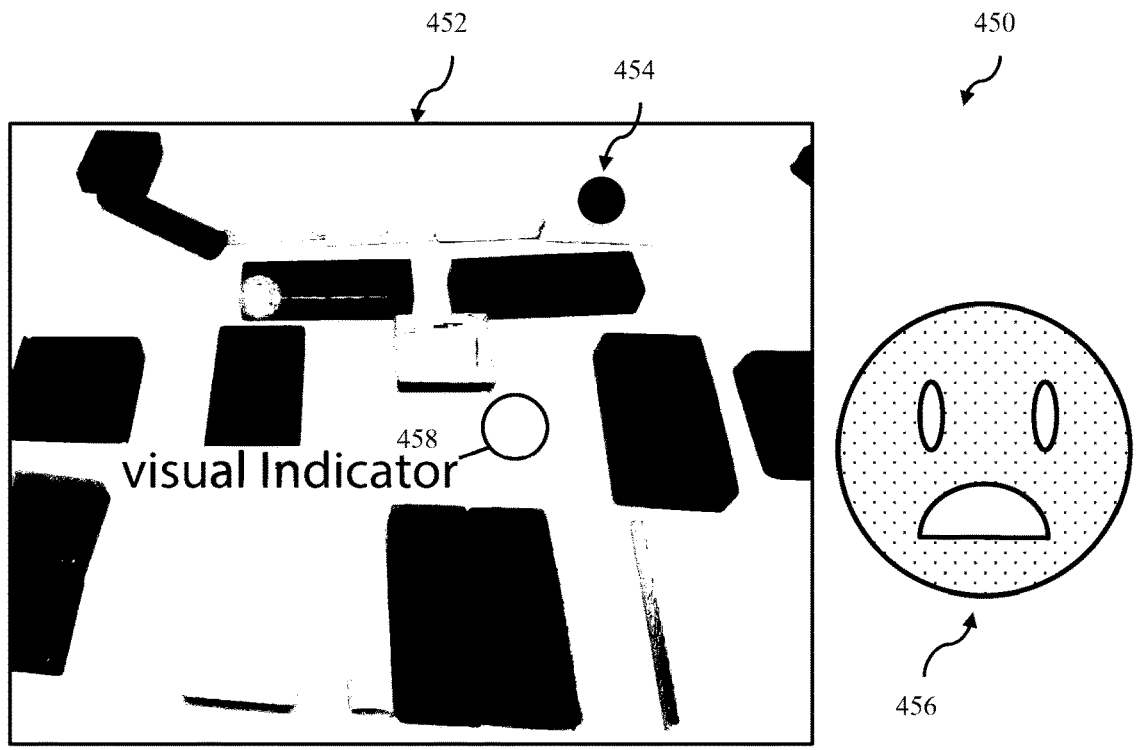
FIG. 4E is representation of the remote user interface.

FIG. 4E is a representation of the remote user interface 450 provided to the remote user 404 in this experiment. In this embodiment the scene (video feed) 452 shows the view of the wooden blocks with the local users gaze directed to the triangle in the upper right corner indicated by gaze indicator 454 in the form of a red circle. The users emotional state is indicated as a negative emoticon face 456 next to the video feed suggesting the local user is unsure which piece to select. In this case the remote user use's a mouse to move the remote user visual indicator 458, which in this case is a green circle, onto the white block in the centre of the field of view.

Figure 5A:
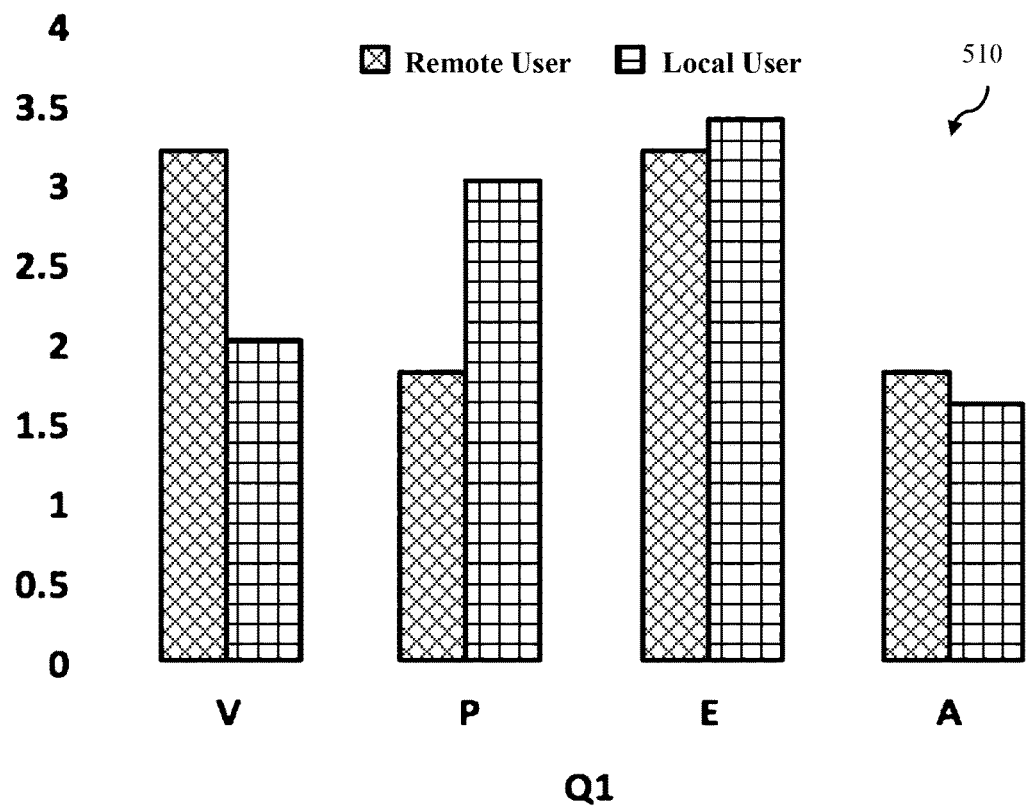
FIG. 5A is a barplot of average rankings from participants in a user trial of an embodiment in response to the question of "which condition did you work best with your partner in"
Figure 5B:
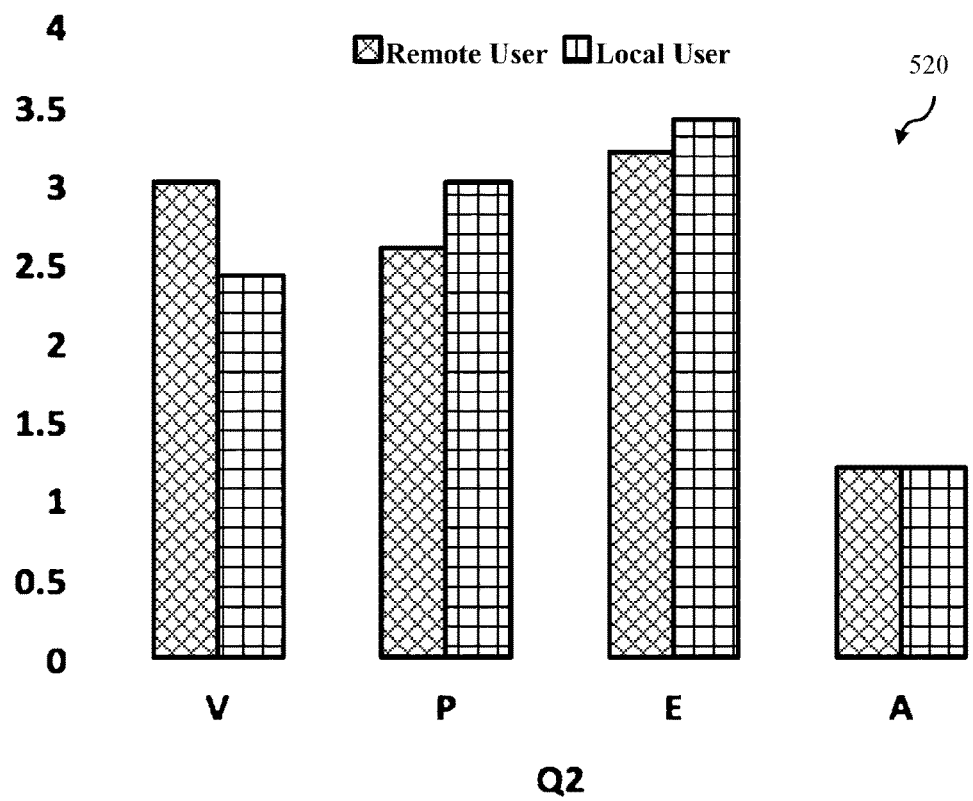
FIG. 5B is a barplot of average rankings from participants in a user trial of an embodiment in response to the question of "which condition did you feel that you communicated best with your partner in"
Figure 5C:
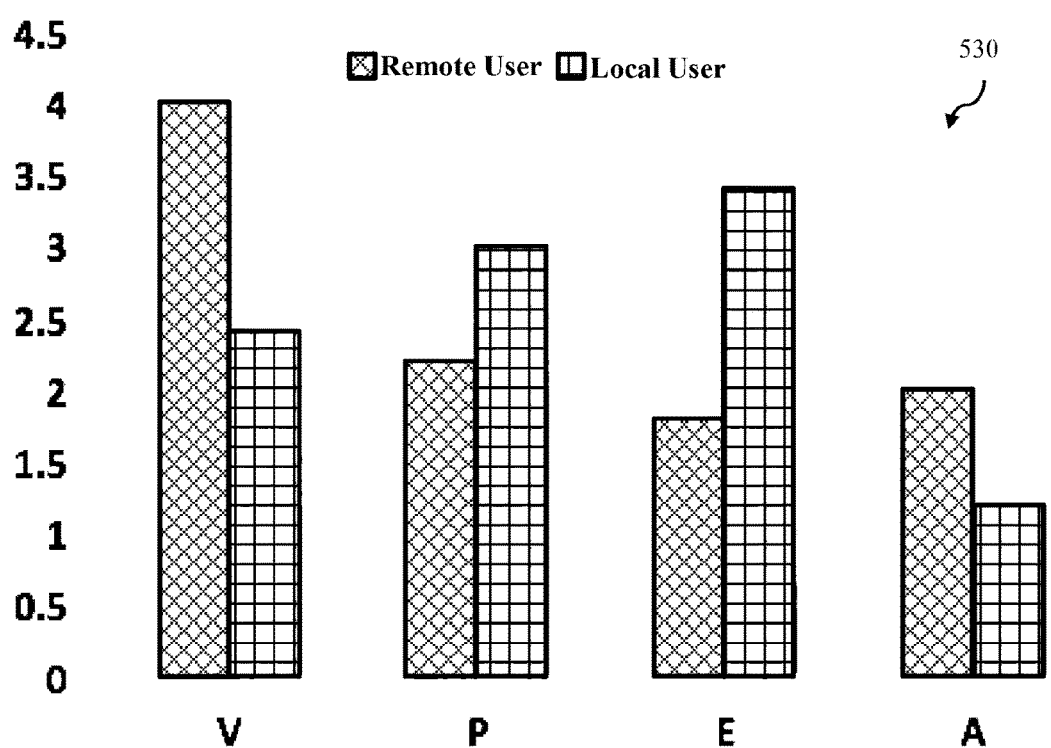
FIG. 5C is a barplot of average rankings from participants in a user trial of an embodiment in response to the question of "which condition did you feel that you understood best how your partner was feeling".

A total of 5 pairs of subjects (6 men, 4 women) completed the pilot test with an age range of 20-45 years old. The subject pairs knew each other as friends or work colleagues and so collaborated together easily. Overall, subjects had no trouble completing the object construction task in the time allocated. There was no significant difference in the average Likert scale scores for each of the conditions for the questions asked. However there was a significant difference in the results to the forced ranking questions. After all the conditions were complete, subjects were asked to rank the four conditions in order from best (1) to worst (4) in response to the following questions; (Q1) Which condition did you work best with your partner in?, (Q2) Which condition did you feel that you communicated best with your partner in?, and (Q3) Which condition did you feel that you under stood best how your partner was feeling? FIGS. 5A to 5C shows the average rankings for each condition for each of these questions. In these figures 1=best, 4=worst, so small column totals indicate better performing conditions. In each condition (V, P, E, A), the left bar is the average scores for the remote user and right bar is the average scores for the local user.

A Friedman test was used to test for significant differences between the results and even with only five pairs of subjects significant differences were found. There was a significant difference between rankings by the local (HMD) users for Q2 ($\chi^2(3)$=8.3, p<0.05) and near significance for the remote users ($\chi^2(3)$=7.3, p=0.06). Similarly there was a significant difference between rankings by the local users for Q3 ($\chi^2(3)$=8.3, p<0.05) and for the remote users ($\chi^2(3)$=9.2, p<0.05). Finally there was a near significant difference in results for Q1 for the local users ($\chi^2(3)$=6.4, p=0.09) and the remote users ($\chi^2(3)$=5.9, p=0.12). After the experiment subjects were interviewed to understand their experience further.

These results indicate that facial expression tracking can be used as an implicit cue to show comprehension. Most interestingly, although the expression (E) and pointing (P) conditions were not rated particularly highly in how well people felt they could communicate with their partner (Q2), the combination of these two conditions (A) was extremely highly ranked, with almost every user rating this as the best. This may be because of the different communication channels offered by each modality. One remote helper stated "I ranked the A condition best, because I could easily point to communicate, and when I needed it I could check the facial expression to make sure I was being understood." Whilst this experiment was a relatively simply construction task which may not cause as much emotional display as other tasks, and only used a single source of physiological data (facial expressions) with a coarse 4 state output, the results clearly indicate that the inclusion of emotional data improved the quality of the collaboration and the ability of the remote helper to assist the local user. In other systems a wider range of physiological data (e.g. heart rate, sweat, audio pitch tracking, etc) could be used to estimate emotional state.

The emotionally aware teleconferencing system described herein enables a remote user to have an increased understanding of what a local user is doing and feeling. When people work face to face they have a good idea of what their partner is doing and how they are feeling (through sharing of verbal and non-verbal cues). However this is typically not the case with most current collaborative technologies and in particular prior art systems. Prior art system lack components such as eye-tracking and emotion/physiological sensing which are integrated into remote collaboration or teleconferencing software. Further the various components of the system can be combined into head worn hardware, such as a system that combines or integrates eye tracking, physiological/emotional sensing and a see through head worn display and camera system. Embodiments of such systems have limited impact on the user as they are relatively light weight, and do not significantly limit what the user can see or hear without the system. For example peripheral vision is not significantly limited. Thus the local wearer is still able to perform typical tasks without any severe limitation. However it is to be understood that additional physiological sensors can also be worn by the user, either on the head, or on other part of the body, to improve the fidelity or accuracy of the estimation of the emotional state of the local wearer. Further embodiments of such systems using non-see through head mounted displays can also be used.

Whilst the embodiments described above are a 1:1 local to remote user configuration, it is to be understood that the system could be extended to other configurations such as 1:many, many:1 and many:many. For example a local user could be monitored by several remote users (i.e. 1:many) potentially each an expert in different areas or by several supervisors. In such embodiments the remote users could be provided with identical interfaces. Control of the detail of annotated data provided to the local user could be either uncoordinated or coordinated. That is each remote user could each decide and control when to change the amount (either increase or decrease) of annotation data provided to the local user. This could be independent of all other remote users. In another embodiment a change to the amount of annotation data to be provided may be coordinated, either in software, or by nominating a master or supervisor remote user who decides when to change the amount based on information received by one or more of the remote users. In this embodiment each remote user could make a suggestion of a change, and the master user can then decide whether to action the change. In another embodiment a software module or agent may receive and act upon suggestions of a change. In the case of conflicting suggestions, the software could force a vote with a majority decision required or use predefined rules to decide how to choose such as based on seniority. Similarly the software could monitor the time since the last change and prevent rapid toggling between changes.

The interface for the local user could be identical to that with a single remote user, for example with a single feed of annotation data, or at least some of the annotation data may be presented in a form which identifies the remote user providing the annotated data. For example different remote users could each have a different coloured and/or shaped indicator (e.g. 3 remote users could user a red circle, green square, purple triangle respectively) used to highlight areas or items in the view of the local user or to provide other visual information. This would allow the user to know who was making the suggestion.

In another embodiment, a remote user could monitor several users such as members of a team sent to an incident site. For example the remote user could be a supervisor in a command and control centre monitoring first responders in the field, or a supervisor or senior technician could monitor multiple field technicians. In one embodiment supporting multiple local users, the remote interface may be portioned into separate portions with each portion displaying a separate local user, or each local user may be displayed in a separate frame, panel, tab or window. The size of the portions/frame/panel/tab/window need not be identical, and the configuration for the interface may be varied depending upon the size. In some embodiments a fixed number of local users are displayed in maximised views and the other local users are displayed in minimised views, and the remote user can toggle local users between minimised and maximised views. In the maximised view the view may show the video feed and provide physiological data and emotional state estimates, and allow annotation of the video feed back to the local user. In the minimised view, a simplified interface may be provided comprising a comparatively smaller video feed e.g., thumbnail sized, and one emotional summary parameter. A summary or control window may also be provided allowing configuration of the remote user interface to control window or portion sizes, data to be displayed in respective maximised and minimised views. The remote user can also control whether they interact with a single user, or with multiple users.

In this embodiment the remote user could be a supervisor at a base location, or a mobile team leader in the field but who is physically remote, that is out of direct site or hearing, from the other members of the team. In other scenarios the remote leader need not be a team leader but simply another team member such as a nominated "buddy" team member. In some embodiments each team member could view one or more (including all) other team members. In these cases the remote interface may be provided in the head mounted display of a user, and the user may be provided with an input device which can be used to control the remote interface. Further the local users may be displayed in a minimised form to restrict.

Similarly in other embodiments many:many scenarios can be supported. That is multiple local users may be monitored by multiple remote users, with remote in this context being separate from at least one of the local users they are monitoring (note that in this case some of the users being monitored could be nearby the remote user). The interface for the many to many scenarios are extensions of the 1:many and many:1 interfaces.

An emotionally aware teleconferencing system has many potential applications, especially those in which it is important to be aware of a local user's emotional or physiological state when at an incident site. For example, a medical first responder at the scene of the accident could use the technology to get remote assistance from a doctor at a hospital, and the remote doctor could monitor what they are looking at and their stress level to make sure they aren't being overloaded with information. Similarly a mountain biker could use this technology to share a bike ride with a remote friend, enabling them to see what they are doing, and their heart rate and excitement level. The remote viewer could also draw annotations on the user's view to show them where they could be riding the bike. Similarly an emergency services commander in a command and control centre could monitor multiple first responders in the field, or a team could be deployed in which team members monitor other team members.

Those of skill in the art would understand that information and signals may be represented using any of a variety of technologies and techniques. For example, data, instructions, commands, information, signals, bits, symbols, and chips may be referenced throughout the above description may be represented by voltages, currents, electromagnetic waves, magnetic fields or particles, optical fields or particles, or any combination thereof. Those of skill in the art would further appreciate that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The steps of a method or algorithm described in connection with the embodiments disclosed herein may be embodied directly in hardware, in a software module executed by a processor, or in a combination of the two. For a hardware implementation, processing may be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described herein, or a combination thereof. Software modules, also known as computer programs, computer codes, or instructions, may contain a number a number of source code or object code segments or instructions, and may reside in any computer readable medium such as a RAM memory, flash memory, ROM memory, EPROM memory, registers, hard disk, a removable disk, a CD-ROM, a DVD-ROM or any other form of computer readable medium. In the alternative, the computer readable medium may be integral to the processor. The processor and the computer readable medium may reside in an ASIC or related device. The software codes may be stored in a memory unit and executed by a processor. The memory unit may be implemented within the processor or external to the processor, in which case it can be communicatively coupled to the processor via various means as is known in the art.

Throughout the specification and the claims that follow, unless the context requires otherwise, the words "comprise" and "include" and variations such as "comprising" and "including" will be understood to imply the inclusion of a stated integer or group of integers, but not the exclusion of any other integer or group of integers. Further, the term "or" is intended to mean an inclusive "or" rather than an exclusive "or." That is, unless specified otherwise, or clear from the context, the phrase "X uses A or B" is intended to mean any of the natural inclusive permutations. That is, the phrase "X uses A or B" is satisfied by any of the following instances: X uses A; X uses B; or X uses both A and B. In addition, the articles "a" and "an" as used in this application and the appended claims should generally be construed to mean "one or more" unless specified otherwise or clear from the context to be directed to a singular form.

Throughout the specification and the claims that follow, unless the context requires otherwise, the words "comprise" and "include" and variations such as "comprising" and "including" will be understood to imply the inclusion of a stated integer or group of integers, but not the exclusion of any other integer or group of integers.

The reference to any prior art in this specification is not, and should not be taken as, an acknowledgment of any form of suggestion that such prior art forms part of the common general knowledge.

It will be appreciated by those skilled in the art that the disclosure is not restricted in its use to the particular application or applications described. Neither is the present disclosure restricted in its preferred embodiment with regard to the particular elements and/or features described or depicted herein. It will be appreciated that the disclosure is not limited to the embodiment or embodiments disclosed, but is capable of numerous rearrangements, modifications and substitutions without departing from the scope as set forth and defined by the following claims.

What is claimed is:

1. A remote user teleconferencing apparatus for use in a teleconferencing system for providing remote assistance to, or monitoring of, at least one local user by a remote user, the apparatus comprising:

a remote user computer apparatus comprising a processor, a memory and a communications module;

a display; and a user input device, wherein the communications module is configured to receive teleconference data from the local user, and the display is configured to display a representation of video data from a camera worn by the at least one local user overlaid with an indication of an eye gaze direction of the respective local user generated from the received teleconference data, and a representation of the respective local user's emotional state, and the user input device is configured to allow the remote user to generate or provide annotation information which are transmitted to the respective local user for display on a head mounted display of the respective local user, wherein the display of an item of annotation information is controlled based upon the respective local user's emotional state;

wherein the remote user apparatus is configured to allow the remote user to control whether an item of annotation information is displayed based upon the respective local user's emotional state.

2. The remote user teleconferencing apparatus of claim 1, wherein the communications module receives an estimate of the local user's emotional state generated by a local user apparatus, wherein the estimate is an emotional state selected from a plurality of predefined emotional states known to both the local user apparatus and remote user teleconferencing apparatus.

3. The remote user teleconferencing apparatus of claim 1, wherein the remote user teleconferencing apparatus is configured to process data from the one or more physiological sensors to generate an estimate of the local user's emotional state.

4. The remote user teleconferencing apparatus of claim 1 wherein the display is a head mounted display worn by the remote user and the remote user teleconferencing apparatus further comprises a headset.

5. A remote user teleconferencing apparatus for use in a teleconferencing system for providing remote assistance to, or monitoring of, at least one local user by a remote user, the apparatus comprising:

a remote user computer apparatus comprising a processor, a memory and a communications module;

a display; and a user input device, wherein the communications module is configured to receive teleconference data from the local user, and the display is configured to display a representation of video data from a camera worn by the at least one local user overlaid with an indication of an eye gaze direction of the respective local user generated from the received teleconference data, and a representation of the respective local user's emotional state, and the user input device is configured to allow the remote user to generate or provide annotation information which are transmitted to the respective local user for display on a head mounted display of the respective local user, wherein the display of an item of annotation information is controlled based upon the respective local user's emotional state;

wherein each item of annotations information has a predefined priority level or is assigned a priority level by the remote user, and each priority level is associated with an emotional state threshold, such that if the estimated emotional state exceeds the emotional state threshold of a priority level, the annotation data associated with that priority level is hidden from the local user, and when the emotional state drops below the emotional state threshold of a priority level the annotation data associated with that priority level is display to the local user.

6. A teleconferencing system for providing remote assistance to, or monitoring of, at least one local user by at least one remote user, the system comprising:

a local user teleconferencing apparatus for each of the at least one local user comprising:

a wearable camera for providing a video feed from the local user's perspective;

a head mounted display;

an eye tracking system mounted to or included in the head mounted display;

a headset;

one or more physiological sensors for monitoring one or more physiological parameters of the local user; and a local user computer apparatus comprising a memory, a processor and a wireless communications module, wherein the computing apparatus is worn or held by the remote user and operatively connected to the wearable camera, headset, head mounted display, eye tracking system and the one or more physiological sensors;

a remote user teleconferencing apparatus comprising:

a remote user computer apparatus for each of the at least one remote user comprising a processor, a memory, and a communications module;

a remote user display; and a user input device, wherein each local user teleconferencing apparatus is configured to transmit teleconferencing data to the at least one remote user teleconferencing apparatus over at least one communication link and each remote user teleconferencing apparatus receiving the teleconferencing data is configured to display a representation of video data from wearable camera overlaid with an indication of an eye gaze direction of the respective local user generated from the eye tracking system, and an estimate of the local user's emotional state is generated with a representation of the respective local user's emotional state from the one or more physiological sensors, and the user input device is configured to allow the remote user to generate one or more annotations on the display which are transmitted to the respective local user for display on the head mounted display of the respective local user, wherein the display of an item of annotation information is controlled based upon the estimate of the local user's emotional state;

wherein the estimate of the local user's emotional state is generated by either the local user computer apparatus or the remote user computer apparatus, and the remote user controls whether an item of annotation information is displayed based upon the estimated user's emotional state.

7. The teleconferencing system as claimed claim 6, wherein the local user computer apparatus comprises instructions for:

analysing, by the local user computer apparatus, data from the one more physiological sensors and estimating an emotional state of the local user; and transmitting the estimated emotional state to the remote user.

8. The teleconferencing system as claimed in claim 7 wherein analysing, by the local user computer apparatus, data from the one more physiological sensors and estimating an emotional state of the local user comprises mapping the data from the one more physiological sensors to one of a plurality of predefined emotional states.

9. The teleconferencing system as claimed in claim 6, wherein the local user computer apparatus is configured to pre-process data from the one more physiological sensors and to transmit the pre-processed data to the remote user, and the remote user computer apparatus is configured to analyse the pre-processed data to obtain an estimate of the emotional state of the local user.

10. A teleconferencing system for providing remote assistance to, or monitoring of, at least one local user by at least one remote user, the system comprising:

a local user teleconferencing apparatus for each of the at least one local user comprising:
a wearable camera for providing a video feed from the local user's perspective;
a head mounted display;
an eye tracking system mounted to or included in the head mounted display;
a headset;
one or more physiological sensors for monitoring one or more physiological parameters of the local user; and
a local user computer apparatus comprising a memory, a processor and a wireless communications module, wherein the computing apparatus is worn or held by the remote user and operatively connected to the wearable camera, headset, head mounted display, eye tracking system and the one or more physiological sensors;
a remote user teleconferencing apparatus comprising:
a remote user computer apparatus for each of the at least one remote user comprising a processor, a memory, and a communications module;
a remote user display; and
a user input device,
wherein each local user teleconferencing apparatus is configured to transmit teleconferencing data to the at least one remote user teleconferencing apparatus over at least one communication link and each remote user teleconferencing apparatus receiving the teleconferencing data is configured to display a representation of video data from wearable camera overlaid with an indication of an eye gaze direction of the respective local user generated from the eye tracking system, and an estimate of the local user's emotional state is generated with a representation of the respective local user's emotional state from the one or more physiological sensors, and the user input device is configured to allow the remote user to generate one or more annotations on the display which are transmitted to the respective local user for display on the head mounted display of the respective local user, wherein the display of an item of annotation information is controlled based upon the estimate of the local user's emotional state;
wherein the estimate of the local user's emotional state is generated by either the local user computer apparatus or the remote user computer apparatus, and each of the one or more annotations has a predefined priority level or is assigned a priority level by the remote user, and each priority level is associated with an emotional state threshold, such that if the estimated emotional state exceeds the emotional state threshold of a priority level, the annotation data associated with that priority level is hidden from the local user, and when the emotional state drops below the emotional state threshold of a priority level the annotation data associated with that priority level is display to the local user.

11. A method for providing remote assistance to, or monitoring of, a local user by a remote user, the method comprising:
generating an estimate of the local user's emotional state and generating a representation of the local user's emotional state from one or more physiological sensors worn by the local user;
generating an eye gaze direction of the local user generated from an eye tracking system worn by the local user; and
displaying, on a display apparatus, to the remote user a representation of video data from a camera worn by the local user overlaid with an indication of the eye gaze direction of the local user and the representation of the local user's emotional state;
generating, by the remote user, one or more annotations which are transmitted to and displayed on a head mounted display of the local user, wherein the display of an item of annotation information is controlled based upon the estimate of the local user's emotional state; and
wherein the remote user controls whether an item of annotation information is displayed based upon the estimated user's emotional state.

12. The method as claimed in claim 11, wherein generating an estimate of the local user's emotional state and generating a representation of the local user's emotional state further comprises:
collecting data from the one or more physiological sensors worn by the local user;
analysing the collected data by a processing apparatus local to the local user and estimating an emotional state of the local user;
transmitting the estimated emotional state to the remote user; and
generating a representation of the local user's emotional state using the received estimated emotional state.

13. The method as claimed in claim 12 wherein the step of analysing the collected data comprises mapping the collected physiological data to one of a plurality of pre-defined emotional states.

14. The method as claimed in claim 12 wherein the step of analysing the collected data comprises mapping the collected physiological data to one of a plurality of pre-defined emotional states using either a neural network, a finite state machine or a machine learning implementation.

15. The method as claimed in claim 11, where the method further comprises:
collecting data from the one or more physiological sensors worn by the local user;
locally pre-processing the collected data;
transmitting the pre-processed data to the remote user;
processing, by a processing apparatus, the received pre-processed data to obtain an estimate of the emotional state of the local user.

16. The method as claimed in claim 11, wherein the remote user monitors a plurality of local users and the generation steps are performed for each user, and the representation step is performed for each user.

17. A method for providing remote assistance to, or monitoring of, a local user by a remote user, the method comprising:
generating an estimate of the local user's emotional state and generating a representation of the local user's emotional state from one or more physiological sensors worn by the local user;
generating an eye gaze direction of the local user generated from an eye tracking system worn by the local user; and
displaying, on a display apparatus, to the remote user a representation of video data from a camera worn by the local user overlaid with an indication of the eye gaze direction of the local user and the representation of the local user's emotional state;
generating, by the remote user, one or more annotations which are transmitted to and displayed on a head mounted display of the local user, wherein the display of an item of annotation information is controlled based upon the estimate of the local user's emotional state;

wherein each of the one or more annotations has a predefined priority level or is assigned a priority level by the remote user, and each priority level is associated with an emotional state threshold, such that if the estimated emotional state exceeds the emotional state threshold of a priority level, the annotation data associated with that priority level is hidden from the local user, and when the emotional state drops below the emotional state threshold of a priority level the annotation data associated with that priority level is display to the local user.

* * * * *